United States Patent [19]
Pissiotas

[11] 3,940,412
[45] Feb. 24, 1976

[54] 2,4,5-TRICHLORO- AND 2,4,5-TRIBROMOIMIDAZOLE DERIVATIVES AND PESTICIDAL COMPOSITIONS CONTAINING THEM

[75] Inventor: Georg Pissiotas, Loerrach, Germany
[73] Assignee: Ciba-Geigy AG, Switzerland
[22] Filed: June 23, 1970
[21] Appl. No.: 49,183

[30] Foreign Application Priority Data
July 4, 1969    Switzerland...................... 10262/69

[52] U.S. Cl.,................................ 260/309; 424/273
[51] Int. Cl.²...................................... C07D 233/68
[58] Field of Search .................................. 260/309

[56] References Cited
UNITED STATES PATENTS
3,423,420    1/1969    Buchel et al........................ 260/309

FOREIGN PATENTS OR APPLICATIONS
1,088,895    10/1967    United Kingdom................. 260/309
1,567,374    5/1969    France............................... 260/309
6,407,401    1/1965    Netherlands....................... 260/309

*Primary Examiner*—Natalie Trousof
*Attorney, Agent, or Firm*—Wenderoth, Lind & Ponack

[57] ABSTRACT

The present invention provides compounds of the formula

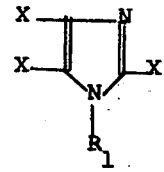

in which X represents chlorine and $R_1$ represents unsubstituted alkenyl of 2 to 4 carbon atoms or chloro substituted alkenyl of 2 to 4 carbon atoms or in which X represents bromine and $R_1$ represents vinyl-, chloro substituted allyl-, or methallyl-, butenyl or chloro substituted butenyl. The novel compounds are useful for combatting representatives of the order Acarina.

3 Claims, No Drawings

2,4,5-TRICHLORO- AND 2,4,5-TRIBROMOIMIDAZOLE DERIVATIVES AND PESTICIDAL COMPOSITIONS CONTAINING THEM

This invention relates to 2,4,5-trichloro- and 2,4,5-tribromoimidazole derivatives and to pesticidal compositions containing them.

The present invention provides compounds of the formula

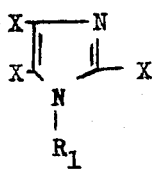

in which X represents a chlorine atom and $R_1$ represents a substituted or unsubstituted alkenyl group having from 2 to 4 carbon atoms or a benzyl group which may be substituted at the phenyl nucleus, or in which X represents a bromine atom and $R_1$ represents a substituted or unsubstituted vinyl group, a substituted alkenyl group having 3 or 4 carbon atoms or a benzyl group which is substituted at the phenyl nucleus.

Accordingly, possible compounds are, for example, (a)

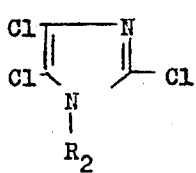

in which $R_2$ represents a substituted or unsubstituted alkenyl group having from 2 to 4 carbon atoms or a benzyl group which may be substituted at the phenyl nucleus, and (b)

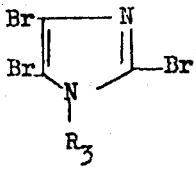

in which $R_3$ represents a substituted or unsubstituted vinyl group, a substituted alkenyl group having 3 or 4 carbon atoms or a benyl group which is substituted at the phenyl nucleus.

The trichloroimidazoles and tribromoimidazoles of the present invention can be manufactured according to methods which are in themselves known and have already been described in detail in the literature, for example, by reaction of an imidazole of the formula

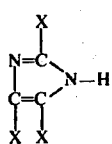

with a halide of the formula R—Hal, preferably in the presence of an acid-binding agent, X and R having the above specified meanings, and Hal represents a fluorine, chlorine, bromine or iodine atom, preferably a chlorine or bromine atom.

Suitably acid-binding agents are, for example, alkali carbonates and alkali alcoholates.

The compounds of the present invention are mainly suitable for combatting representatives of the order Acarina, for example, mites and ticks, as well as all their stages of development, such as eggs, larvae and pupae. Representatives of the order Acarina are, for example, Eulaelaps; Echninolaelaps; Laelaps; Haemogamasus, Dermanyssus; Ornithonyssus; Allodermanyssus, especially Allodermanyssus sanguineus; Pneumonyssus; Amblyomma; Aponomma; Boophilus; Dermacentor; Haemophysalis Hyalomma; Ixodidae; Margaropus; Rhipicephalus; Ornithodorus; Otobius; Cheyletidae, for example, Cheyletus; Psorergates; Demodicidae; Trombiculidae for example Trombicula; Eutrombicula; Schongastia; Acomatacurus; Neoschongastia, Euschongastia; Sarcoptiformes, for example, Notoedres; Sarcoptes; Knemidokoptes; Psoroptidae, for example, Psoroptes, Chloroioptes; Otodectes or Tetranychidae, for example, *Tetranychus telarius* and *Tetranychus urticae*.

Accordingly, the present invention also provides a pesticidal composition which comprises, as active ingredient, at least one compound of the general formula.

The compounds of the present invention can be employed by themselves or together with suitable carriers and/or additives. Suitable carriers and additives can be solid or liquid and correspond to the substances which are customary in formulation technology, for example, natural or regenerated substances, solvents, dispersing agents, wetting agents, adhesives, thickeners, binders and/or fertilisers. Furthermore, other insecticidally or acaricidally active compounds can be added, for example,

PHOSPHORIC ACID DERIVATIVES

Bis-O,O-diethylphosphoric acid anhydride (TEPP)
O,O,O,O-Tetrapropyldithiopyrophosphate
Dimethyl(2,2,2-trichloro-1-hydroxyethyl)phosphonate (TRICHRORFON)
1,2-Dibromo-2,2-dichloroethyldimethylphosphate (NALED)
2,2-Dichlorovinyldimethylphosphate (DICHLORFOS)
2-Methoxycarbamyl-1-methylvinyldimethylphosphate (MEVINPHOS)
Dimethyl-1-methyl-2-(methylcarbamoyl)vinylphosphate cis (MONOCROTOPHOS)
3-(Dimethoxyphosphinyloxy)-N-methyl-N-methoxy-cis-crotonamide
3-(Dimethoxyphosphinyloxy)-N,N-dimethyl-cis-crotonamide (DICROTOPHOS)
2-Chloro-2-diethylcarbamoyl-1-methylvinyldimethylphosphate (PHOSPHAMIDON)
O,O-Diethyl-O-2-(ethylthio)-ethylthiophosphate (DEMETON)
O,O-Diethyl-S-2-(ethylthio)-ethylthiophosphate
S-Ethylthioethyl-O,O-dimethyl-dithiophosphate (THIOMETON)
O,O-Diethyl-S-ethylmercaptomethyldithiophosphate (PHORATE)
O,O-Diethyl-S-2-[(ethylthio)ethyl]dithiophosphate (DISULFOTON)

O,O-Dimethyl-S-2-(ethylsulphinyl)ethylthiophosphate (OXYDEMETONMETHYL)
O,O-Dimethyl-S-(1,2-dicarbethoxyethyl)dithiophosphate (MALATHION)
(O,O,O,O-Tetraethyl-S,S'-methylene-bis-[dithiophosphate] (ETHION)
O-Ethyl-S,S-dipropyldithiophosphate
O,O-Dimethyl-S-(N-methyl-N-formylcarbamoylmethyl)-dithiophosphate (FORMOTION)
O,O-Dimethyl-S-(N-methylcarbamoylmethyl)dithiophosphate (DIMETHAT)
O,O-Dimethyl-S-(N-ethylcarbamoylmethyl)dithiophosphate (ETHOATMETHYL)
O,O-Diethyl-S-(N-isopropylcarbamoylmethyl)-dithiophosphate (PROTHOAT)
S-N-(1-Cyano-1-methylethyl)carbamoylmethyldiethylthiolphosphate (CYANTHOAT)
S-(2-Acetamidoethyl)-O,O-dimethyldithiophosphate
Hexamethylphosphoric acid triamide (HEMPA)
O,O-Dimethyl-O-p-nitrophenylthiophosphate (PARATHION-METHYL)
O,O-Diethyl-O-p-nitrophenylthiophosphate (PARATHION)
O-Ethyl-O-p-nitrophenylthiophosphonate (EPN)
O,O-Dimethyl-O-(4-nitro-m-tolyl)thiophosphate (FENITROTHION)
O,O-Dimethyl-O-(2-chloro-4-nitrophenyl)thiophosphate (DICAPTHON)
O,O-Dimethyl-O-p-cyanophenylthiophosphate (CYANOX)
O-Ethyl-O-p-cyanophenylphenylthiophosphonate
O,O-Diethyl-O-2,4-dichlorophenylthiophosphate (DICHROFENTHION)
O-2,4-Dichlorophenyl-O-methylisopropylamidothiophosphate
O,O-Dimethyl-O-2,4,5-trichlorophenylthiophosphate (RONNEL)
O-Ethyl-O-2,4,5-trichlorophenylethylthiophosphonate (TRICHLORONAT)
O,O-Dimethyl-O-2,5-dichloro-4-bromophenylthiophosphate (BROMOPHOS)
O,O-Diethyl-O-2,5-dichloro-4-bromophenylthiophosphate (BROMOPHOS-ETHYL)
O,O-Dimethyl-O-(2,5-dichlor-4-iodophenyl)-thiophosphate (IODOFENPHOS)
4-tert. Butyl-2-chlorophenyl-N-methyl-O-methylamidophosphate (CRUFOMAT)
Dimethyl-p-(methylthio)phenylphosphate
O,O-Dimethyl-O-(3-methyl-4-methylmercaptophenyl)thiophosphate (FENTHION)
Isopropylamino-O-ethyl-O-(4-Methylmercapto-3-methylphenyl)-phosphate
O,O-Diethyl-O-p-[(methylsulphinyl)phenyl]-thiophosphate (FENSULFOTHION)
O,O-Dimethyl-O-p-sulphamidophenylthiophosphate
O-[p-(Dimethylsulphamido)phenyl]O,O-dimethylthiophosphate (FAMPHUR)
O,O,O',O'-Tetramethyl-O,O'-thiodi-p-phenylenethiophosphate
O-(p-(p-Chlorophenyl)azophenyl)O,O-dimethylthiophosphate (AZOTHOAT)
O-Ethyl-S-phenyl-ethyldithiophosphonate
O-Ethyl-S-4-chlorophenyl-ethyldithiophosphonate
O-Isobutyl-S-p-chlorophenyl-ethyldithiophosphonate
O,O-Dimethyl-S-p-chlorophenylthiophosphate
O,O-Dimthyl-S-(p-chlorophenylthiomethyl)-dithiophosphate
O,O-Diethyl-p-chlorophenylmercaptomethyl-dithiophosphate (CARBOPHENOTHION)
O,O-Diethyl-S-p-chlorophenylthiomethyl-thiophosphate
O,O-Dimethyl-S-(carbethoxy-phenylmethyl)dithiophosphate (PHENOTHOAT)
O,O-Diethyl-S-(carbofluorethoxy-phenylmethyl)-dithiophosphate
O,O-Dimethyl-S-(carbisopropoxy-phenylmethyl)-dithiophosphate
O,O-Dimethyl-O-(alpha-methylbenzyl-3-hydroxycrotonyl)phosphate,
2-Chloro-1-(2,4-dichlorophenyl)vinyl-diethylphosphate (CHLORFENVINPHOS)
2-Chloro-1-(2,4,5-trichlorophenyl)vinyl-dimethylphosphate
O-(2-Chloro-1-(2,5-dichlorophenyl)vinyl)-O,O-diethylthiophosphate
Phenylglyoxylonitriloxime-O,O-diethylthiophosphate (PHOXIM)
O,O-Diethyl-O-(3-chloro-4-methyl-2-oxo-2-H-1-benzopyran-7-yl)-thiophosphate (COUMAPHOS)
O,O-Diethyl-7-hydroxy-3,4-tetramethylene-coumarinyl-thiophosphate (COUMITHOAT)
2,3-p-Dioxanedithiol-S,S-bis(O,O-diethyldithiophosphate) (DIOXATHION)
2-Methoxy-4-H-1,3,2-benzodioxaphosphorine-2-sulphide
O,O-Diethyl-O-(5-phenyl-3-isooxyzolyl (sic)) thiophosphate
S-[(6-Chloro-2-oxo-3-benzoxazolinyl)methyl]O,O-diethyldithiophosphate (PHOSALON)
2-(Diethoxyphosphinylimino)-4-methyl-1,3-dithiolane
O,O-Dimethyl-S-[2-methoxy-1,3,4-thiadiazol-5-(4H)-onyl-(4)-methyl]dithiophosphate
Tris-(2-methyl-1-aziridinyl)-phosphine-oxide (METEPA)
O,O-Dimethyl-S-phthalimidomethyl-dithiophosphate
S-(2-Chloro-1-phthalimidoethyl)-O,O-diethyldithiophosphate
N-Hydroxynaphthalimido-diethylphosphate
Dimethyl-3,5,6-trichloro-2-pyridylphosphate
O,O-Dimethyl-O-(3,5,6-trichloro-2-pyridyl)thiophosphate
O,O-Diethyl-O-(3,5,6-trichloro-2-pyridyl)thiophosphate
O,O-Diethyl-O-2-pyrazinylthiophosphate (THIONAZIN)
O,O-Diethyl-O-(2-isopropyl-4-methyl-6-pyrimidyl)-thiophosphate (DIAZINON)
O,O-Diethyl-O-(2-quinoxylyl)thiophosphate
O,O-Dimethyl-S-(4-oxo-1,2,3-benzotriazin-3(4H)-ylmethyl)-dithiophosphate (AZINPHOSMETHYL)
O,O-Diethyl-S-(4-oxo-1,2,3-benzotriazin-3(4H)-ylmethyl)-dithiophosphate (AZINPHOSETHYL)
S-[(4,6-Diamino-s-triazin-2-yl)methyl]-O,O-dimethyldithiophosphate (MENAZON)
S-[2-(Ethylsulphonyl)ethyl]dimethylthiolphosphate (DIOXYDEMETON-S-METHYL)
Diethyl-S-[2-(ethylsulphinyl)ethyl]dithiophosphate (OXYDISULFOTON)
Bis-O,O-diethylthiophosphoric acid anhydride (SULFOTEP)
Dimethyl-1,3-di(carbomethoxy)-1-propen-2-yl-phosphate Dimethyl-(2,2,2-trichloro-1-butyroyloxyethyl)phosphonate (BUTONAT)
O,O-Dimethyl-O-(2,2-dichloro-1-methoxy-vinyl)-phosphate
O,O-Dimethyl-O-(3-chloro-4-nitrophenyl)thiophosphate (CHLORTHION)
O,O-Dimethyl-O(or S)-2-(ethylthioethyl)thiophosphate (DEMETON-S-METHYL)
Bis-(dimethylamido)fluorophosphate (DIMEFOX)
2-(O,O-Dimethyl-phosphoryl-thiomethyl)-5-methoxy-pyrone-4
3,4-Dichlorobenzyl-triphenylphosphonium chloride
Dimethyl-N-methoxymethylcarbamoylmethyl-dithiophosphate (FORMOCARBAM)
O,O-Diethyl-O-(2,2-dichloro-1-chlorethoxyvinyl)-phosphate
O,O-Dimethyl-O-(2,2-dichloro-1-chlorethoxyvinyl)-phosphate
O-Ethyl-S,S-diphenyldithiolphosphate
O-Ethyl-S-benzyl-phenyldithiophosphonate
O,O-Diethyl-S-benzyl-thiolphosphate
O,O-Dimethyl-S-(4-chlorophenylthiomethyl)dithiophosphate (METHYLCARBOPHENOTHION)
O,O-Dimethyl-S-(ethylthiomethyl)dithiophosphate
Diisopropylaminofluorophosphate (MIPAFOX)
O,O-Dimethyl-S-(morpholinylcarbamoylmethyl)dithiophosphate (MORPHOTHION)
Bismethylamido-phenylphosphate
O,O-Dimethyl-S-(benzenesulphonyl)dithiophosphate
O,O-Dimethyl-(S and O)-ethylsulphinylethylthiophosphate
O,O-Diethyl-O-4-nitrophenylphosphate
O,O-Diethyl-S-(2,5-dichlorophenylthiomethyl)dithiophosphate (PHENDAPTON)
Triethoxy-isopropoxy-bis (thiophosphinyl)disulphide
O,O-Diethyl-O-(4-methyl-coumarinyl-7)-thiophosphate (POTASAN)
2-Methoxy-4H-1,3,2-benzodioxaphosphorine-2-oxide
Octamethylpyrophosphoramide (SCHRADAN)
Bis(dimethoxythiophosphinylsulphido)-phenylmethane
5-Amino-bis(dimethylamino)phosphinyl-3-phenyl-1,2,4-triazole (TRIAMIPHOS)
N-Methyl-5-(O,O-Dimethylthiolphosphoryl)-3-thiavaleramide (VAMIDOTHION) and
N,N,N',N'-Tetramethyldiamidofluorophosphate (DIMEFOX)

CARBAMIC ACID DERIVATIVES

1-Naphthyl-N-methylcarbamate (CARBARYL)
2-Butinyl-4-chlorophenylcarbamate
4-Dimethylamino-3,5-xylyl-N-methylcarbamate
4-Dimethylamino-3-tolyl-N-methylcarbamate (AMINOCARB)
4-Methylthio-3,5-xylyl-N-methylcarbamate (METHIOCARB)
3,4,5-Trimethylphenyl-N-methylcarbamate
2-Chlorophenyl-N-methylcarbamate (CPMC)
5-Chlor-6-oxo-2-norbornane-carbonitrile-O-(methylcarbamoyl)-oxime
1-(Dimethylcarbamoyl)-5-methyl-3-pyrazolyl-N,N-dimethylcarbamate (DIMETILAN)
2,3-Dihydro-2,2,-dimethyl-7-benzofuranyl-N-methylcarbamate (CARBOFURAN)
2-Methyl-2-methylthio-propionaldehyde-O-(methylcarbamoyl)oxime (ALDICARB)
8-Quinaldyl-N-methylcarbamate and its salts
Methyl 2-isopropyl-4-(methylcarbamoyloxy)carbanilate
m-(1-Ethylpropyl)phenyl-N-methylcarbamate
3,5-Di-tert.butyl-N-methylcarbamate
m-(1-Methylbutyl)phenyl-N-methylcarbamate
2-Isopropylphenyl-N-methylcarbamate
2-sec.Butylphenyl-N-methylcarbamate
m-Tolyl-N-methylcarbamate
2,3-Xylyl-N-methylcarbamate
3-Isopropylphenyl-N-methylcarbamate
3-tert.Butylphenyl-N-methylcarbamate
3-sec.-Butylphenyl-N-methylcarbamate
3-Isopropyl-5-methylphenyl-N-methylcarbamate (PROMECARB)
3,5-Diisopropylphenyl-N-methylcarbamate
2-Chlor-5-isopropylphenyl-N-methylcarbamate
2-Chloro-4,5-dimethylphenyl-N-methylcarbamate
2-(1,3-Dioxolan-2-yl)phenyl-N-methylcarbamate (DIOXYCARB)
2-(4,5-Dimethyl-1,3-dioxolan-2-yl)phenyl-N-methylcarbamate
2-(1,3-Dioxan-2-yl)phenyl-N-methylcarbamate
2-(1,3-Dithiolan-2-yl)phenyl-N-methylcarbamate
2-(1,3-Dithiolan-2-yl)phenyl-N,N-dimethylcarbamate
2-Isopropoxyphenyl-N-methylcarbamate (ARPROCARB)
2-(2-Propinyloxy)phenyl-N-methylcarbamate
2-(2-Propinyloxy)phenyl-N-methylcarbamate
3-(2-Propinyloxy)phenyl-N-methylcarbamate
2-Dimethylaminophenyl-N-methylcarbamate
2-Diallylaminophenyl-N-methylcarbamate
4-Diallylamino-3,5-xylyl-N-methylcarbamate (ALLYXICARB)
4-Benzothienyl-N-methylcarbamate
2,3-Dihydro-2-methyl-7-benzofuranyl-N-methylcarbamate
3-Methyl-1-phenylpyrazol-5-yl-N,N-dimethylcarbamate
1-Isopropyl-3-methylpyrazol-5-yl-N,N-dimethylcarbamate (ISOLAN)
2-(N',N'-Dimethylcarbamoyl)-3-methylpyrazol-5-yl-N,N-dimethylcarbamate
2-Dimethylamino-5,6-dimethylpyrimidin-4-yl-N,N-dimethylcarbamate
3-Methyl-4-dimethylaminomethyleneiminophenyl-N-methylcarbamate
3-Dimethylamino-methyleneiminophenyl-N-methylcarbamate
1-Methylthio-ethylimino-N-methylcarbamate (METHOXYMYL)
2-Methylcarbamoyloxyimino-1,3-dithiolane
5-Methyl-2-methylcarbamoyloxyimino-1,3-oxathiolane
2-(1-Methoxy-2-propoxy)phenyl-N-methylcarbamate
2-(1-Butin-3-yl-oxy)phenyl-N-methylcarbamate
3-Methyl-4-(dimethylamino-methylmercapto-methyleneimino) phenyl-N-methylcarbamate
1,3-Bis(carbamoylthio)-2-(N,N-dimethylamino)-propane hydrochloride
5,5-Dimethylhydroresorcinoldimethylcarbamate
2-[Propargylethylamino]-phenyl-N-methylcarbamate
2-[Propargylmethylamino]-phenyl-N-methylcarbamate
2-[Dipropargylamino]-phenyl-N-methylcarbamate 3-Methyl-4-[dipropargylamino]-phenyl-N-methyl-carbamate 3,5-Dimethyl-4-[dipropargylamino]-phenyl-N-methylcarbamate
2-[Allyl-isopropylamino]-phenyl-N-methylcarbamate and
3-[Allyl-isopropylamino]-phenyl-N-methylcarbamate.

CHLORINATED HYDROCARBONS

γ-Hexachlorocyclohexane [Gammerxane; Lindane; γ HCH]
1,2,4,5,6,7,8,8-Octachloro-3α,4, 7, 7α'-tetrahydro-4,7-methyleneindane [Chlordan]
1,4,5,6,7,8,8-Heptachloro-3α,4,7,7α-tetrahydro-4,7-methyleneindane [Heptachlor]
1,2,3,4,10,10-Hexachloro-1,4,4α,5,8,8α-hexahydro-endo-1,4-exo-5,8-dimethanonaphthalene [Aldrin]
1,2,3,4,10,10-Hexachlor-6,7-epoxy-1,4,4α,5,6,7,8-,8α,9-octahydro-exo-1,4-endo-5,8-dimethanonaphthalene [Dieldrin] ditto, endo-endo- [Endrin]
6,7,8,9,10,10-Hexachloro-1,5,5α,6,9,9α-hexahydro-6,9-methano-2,3,4 benzo[e]-dioxa-thiepene-3-oxide [Endosulfan]
Chlorinated camphor [Toxaphen]
Decachloroctahydro-1,3,4-metheno-2H-cyclobuta[e d] pentalen-2-one
Dodecachloroctahydro-1,3,4-metheno-1H-cyclobuta[c d]pentalene [Mirex]
Ethyl-1,1α,3,3α,4,5,5α,5α,6-decachloroctahydro-2-hydroxy-1,3,4-metheno-1H-cyclobuta[c d]pentalene-2-laevulinate
Bis(pentachloro-2,4-cyclopentadien-1-yl)
Dinoctone-o
1,1,1-Trichloro-2,2-bis(p-chlorophenyl)ethane [DDT]
Dichlorodiphenyl-dichlorethane [TDE]
Di(p-chlorophenyl)-trichloromethylcarbinol [Dicofol]
Ethyl-4,4'-dichlorophenylglycollate [Chlorobenzylate]
Ethyl-4,4'-dibromobenzylate [Bromobenzylate]
Isopropyl-4,4'-dichlorobenzylate
1,1,1-Trichloro-2,2 bis(p-methoxyphenyl)ethane [Methoxychlor]
Diethyl-diphenyl-dichlorethane
Decachloropentacyclo(3,3,2, $O^{2,6}$, $O^{3,9}$, $O^{7,10}$)decan-4-one [Chlordecon].

NITROPHENOLS AND DERIVATIVES 4,6-Dinitro-6-methylphenol Na salt [dinitrocresol]
Dinitrobutylphenyl-2,2',2''-triethanolamine salt
2-Cyclohexyl-4,6-dinitrophenol [Dinex]
2-(1-Methylheptyl)-4,6-dinitrophenyl-crotonate [Dinocap]
2 sec.-Butyl-4,6-dinitrophenyl-3-methyl-butenoate [Binapacryl]
2 sec.-Butyl-4,6-dinitrophenyl-cyclopropionate and
2 sec.-Butyl-4,6-dinitrophenyl-isopropyl-carbonate [Dinobuton]

VARIOUS SUBSTANCES

Sabadilla
Rotenon
Cevadin
Veratridin
Ryania
Pyrethrin
3-Allyl-2-methyl-4-oxo-2-cyclopenten-1-yl-chrysanthemumate (Allethrin)
6-Chloropiperonyl-chrysanthemumate (Barthrin)
2,4-Dimethylbenzyl-chrysanthemumate (Dimethrin)
2,3,4,5-Tetrahydrophthalimidomethyl-chrysanthemumate (5-Benzyl-3-furyl)-methyl-2,2-dimethyl-3-(2-methylpropanyl) cyclopropanecarboxylate
Nicotine
Bacillus thuringiensis Berliner
Dicyclohexylcarbodiimide
Diphenyldiimide [azobenzene (sic)]
4-Chlorobenzyl-4-chlorophenylsulphide [Chlorobensid]
Creosote oil
6-Methyl-2-oxo-1,3-dithiolo-[4,5-b]-quinoxaline [Quinomethionat]
(I)-3-(2-Furfuryl)-2-methyl-4-oxocyclopent-2-enyl-(I)-(cis+ trans)chrysanthemum-monocarboxylate [Furethrin]
2-Pivaloyl-indane-1,3-dione [Pindon]
2-Fluorethyl(4-bisphenyl)acetate
2-Fluoro-N-methyl-N(1-naphthyl)-acetamide
Pentachlorophenol and salts
2,2,2-Trichloro-N-(pentachlorophenyl)-acetimidoyl chloride
N'-(4-Chloro-2-methylphenyl)-N,N-dimethylformamidine chlorphenamidine)
4-Chlorobenzyl-4-fluorophenyl-sulphide (Fluorobenside)
5,6-Dichloro-1-phenoxycarbanyl-2-trifluoromethyl-benzimidazole (Fenozaflor)
Tricyclohexyl-tin hydroxide
2-Thiocyanatoethyl-lauric acid ester
β-Butoxy-β'-thiocyanatodiethyl-ether
Isobornyl-thiocyanatoacetate
p-Chlorophenyl-p-chlorobenzenesulphonate (Ovex)
2,4-Dichlorophenyl-benzenesulphonate
p-Chlorophenyl-benzenesulphonate (Fenson)
p-Chlorophenyl-2,4,5-trichlorophenylsulphone (Tetradifon)
p-Chlorophenyl-2,4,5-trichlorophenylsulphide (Tetrasul)
Methyl bromide
p-chlorophenyl-phenylsulphone
p-Chlorobenzyl-p-chlorophenylsulphide (Chlorobenside)
4-Chlorophenyl-2,4,5-trichlorophenylazosulphide
2(p-tert.-Butylphenoxy)-1-methylethyl-2-chlorethylsulphite
2(p-tert.-Butylphenoxy)cyclohexyl-2-propinyl-sulphite
4,4'-Dichloro-N-methylbenzenesulphonanilide
N-(2-Fluoro-1,1,2,2-tetrachlorethylthio)-methanesulphonanilid
2-Thio-1,3-dithiolo-(4,5-6)quinoxaline (Thioquinox)
Chloromethyl-p-chlorophenylsulphone (lauseto (sic!) new)
1,3,6,8-Tetranitrocarbazole and
Prop-2-ynyl-(4-t-butylphenoxy)-cyclohexylsulphite (Propargil).

For application, the compounds of the present invention can be processed into dusting agents, emulsion concentrates, granules, dispersions, sprays, solutions or suspensions of the usual formulation.

Suitable substances for the manufacture of directly sprayable solutions of the compounds of the present invention are, for example, mineral oil fractions of high to medium boiling range, such as diesel oil or kerosene, coal tar oils and oils of vegetable or animal origin, as well as hydrocarbons, such as alkylated naphthalenes, or tetrahydronaphthalene, optionally using xylene mixtures, cyclohexanols, ketones and chlorinated hydrocarbons, such as trichlorethane and tetrachlorethane, trichlorethylene or trichlorobenzenes and tetrachlorobenzenes. Organic solvents of boiling point above 100°C are advantageously used.

Aqueous application forms are especially advantageously prepared from emulsion concentrates, pastes or wettable spraying powders by addition of water. Suitable dispersing agents are non-ionic products, for example, condensation products of aliphatic alcohols, amines or carboxylic acids having a long-chain hydrocarbon radical of about 10 to 20 carbon atoms and ethylene oxide, such as the condensation product of octadecyl alcohol and 25 to 30 mols of ethylene oxide, or that of soya fatty acid and 30 mols of ethylene oxide or that of technical oleylamine and 15 mols of ethylene oxide or that of dodecylmercaptan and 12 mols of ethylene oxide. Amongst the anionic dispersing agents which can be employed there may, for example, be mentioned: the sodium salt of dodecyl alcohol sulphuric acid ester, the sodium salt of dodecylbenzenesulphonic acid, the potassium or triethanolamine salt or oleic acid or of abietic acid or of mixtures of these acids, or the sodium salt of a petroleum-sulphonic acid. Suitable cationic dispersing agents are quaternary ammonium compounds, for example, cetylpyridinium bromide or dihydroxyethylbenzyldodecylammonium chloride.

To manufacture dusting agents and sprinkling agents, talc, kaolin, bentonite, calcium carbonate and calcium phosphate, as well as coal, cork powder, wood flour and other materials of vegetable origin can be employed as solid carriers. It is also very appropriate to manufacture preparations in a granular form. The various use forms can, in the customary manner, be provided with addition of substances which improve the distribution, the adhesion, the rain resistance or the penetrating power; such substances are, for example, fatty acids, resins, glue, casein or alginates.

The content of the active ingredient in the compositions described above lies between 0.1 and 95%, and at the same time is should be mentioned that in the case of application from aircraft or by means of other suitable application instruments concentrations of up to 99.5% or even pure active substance can be employed.

The application of these agents in the veterinary field takes place in accordance with the customary processes, for example in accordance with the spraying, pouring, dusting and fumigating process. The so-called dipping process, in which the animal is driven through a solution or dispersion of the agent, is also effective.

The preparations for application in the spraying, pouring and dipping process preferably contain from 0.05% to 0.5% of the active ingredient.

The present invention also provides a method of combatting ticks and mites, which comprises applying thereto a compound of the formula

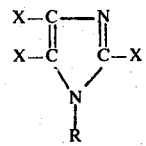

in which X represents a chlorine atom or a bromine atom and R represents an alkyl group having from 1 to 4 carbon atoms an alkenyl group having from 2 to 4 carbon atoms, a phenyl group or a benzyl group which may be substituted at the phenyl nucleus. The alkyl and alkenyl groups which are represented by R can be branched or straight-chain, unsubstituted or substituted. Suitable alkyl and alkenyl groups are, for example, methyl, trifluoromethyl, ethyl, propyl, isopropyl, n-, i-, sec.- and tert.-butyl, vinyl, allyl, methallyl, chlorallyl and methylpropenyl groups. The substituents on the alkyl, alkenyl and phenyl groups and on the phenyl nucleus of the benzyl group can be of the first or second order.

By substituents of the first order there are herein especially meant electron donors which intensify the basicity. Suitable groups for this purpose are, inter alia, the following halogen atoms, for example, fluorine, chlorine, bromine or iodine atoms; alkoxy and alkylthio groups having from 1 to 4 carbon atoms and which can be branched or unbranched, but are preferably unbranched and have 1 or 2 carbon atoms; lower alkoxyalkylene groups; primary, secondary and, especially, tertiary amino groups, with lower alkyl and alkanol groups being preferred substituents; hydroxyl groups and mercapto groups. In the case of the phenyl radicals and the phenyl nucleus of the benzyl group, further possible substituents are alkyl and monohalogenalkyl and dihalogenalkyl groups.

By substituents of the second order, there are herein especially meant acidifying electron donors. Suitable groups are, inter alia, the following: nitroso, nitro and nitrile groups; trihalogenalkyl groups, in which the halogen atoms are preferably fluorine and chlorine atoms; lower alkyl sulphinyl and lower alkylsulphonyl groups, which possess a branched or unbranched alkyl radical having from 1 to 4 carbon atoms, preferably an unbranched alkyl radical having 1 or 2 carbon atoms.

The following Examples illustrate the invention.

EXAMPLE 1

23 g of trichloroimidazole, 12.8 ml of allyl bromide, 20.4 g of potassium carbonate and 150 ml of acetone were boiled overnight under reflux. After cooling, the mixture was filtered and the filtrate was concentrated in vacuo. The residual oil was subjected to fractional distillation, whereupon the compound of formula

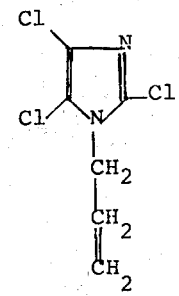

was obtained in the pure form.
Boiling point: 83°C at 0.15 mm Hg. Yield 86%.

The following compounds were manufactured analogously:
Compound No.

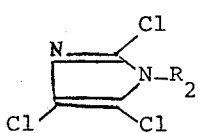

boiling point/melting point, °C

| | | |
|---|---|---|
| 1.2 | —CH₂—C(CH₃)=CH₂ | 85/0.08 mm Hg |
| 1.3 | —CH₂—CH=CHCl | 100/0.13 mm Hg |
| 1.4 | —CH₂—C(Cl)=CH₂ | 104/0.15 mm Hg |

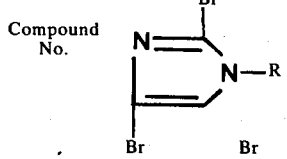

Compound No. / boiling point/melting point °C

| | | |
|---|---|---|
| 2.1 | —CH₂—CH=CH₂ | 120/0.12 mm Hg |
| 2.2 | —CH₂—C(CH₃)=CH₂ | 92/0.04 mm Hg |
| 2.3 | —CH₂—CH=CH—Cl | 84/0.05 mm Hg |
| 2.4 | —CH₂—C(Cl)=CH₂ | 97/0.05 mm Hg |
| 2.5 | —CH₂—CH₂—CH₂—CH₃ | 124/0.06 mm Hg |
| 2.6 | —CH₂—CH₃ | 62 – 64 |
| 2.7 | —CH₂—CH=CH—CH₃ | 120/0.06 mm Hg |
| 2.8 | —CH₃ | 93 – 94.5 |
| 2.9 | —CH₂—CH₂—CH₃ | 74 – 76 |
| 2.10 | —CH₂—CH=C(Cl)—CH₃ | 82 – 83 |
| 2.11 | —CH₂—C₆H₅ | 68–69 |
| 2.12 | —CH₂—(2,6-Cl₂C₆H₃) | 166 – 168 |
| 2.13 | —CH₂—(3,4-Cl₂C₆H₃) | 160 – 162 |
| 2.14 | —CH₂—(3,4-Cl₂C₆H₃) | 91 – 92 |
| 2.15 | —CH₂—(4-ClC₆H₄) | 99 – 100 |
| 2.16 | —CH₂—(3-ClC₆H₄) | 149 – 151 |
| 2.17 | —CH₂—(3,4,?-Cl₃C₆H₂) | 244 – 246 |

EXAMPLE 2

DUSTING AGENTS

Equal parts of an active substance of formula I and of precipitated silica were finely ground. Dusting agents, preferably containing 1–6% of active substance, could be manufactured therefrom by mixing with kaolin or talc.

SPRAYING POWDERS

In order to manufacture a spraying powder, the following components were for example mixed and finely ground:
 50 parts of active substance according to the present invention
 20 parts of highly adsorbent silica
 25 parts of Bolus alba (kaolin)
 1.5 parts of sodium 1-benzyl-2-stearyl-benzimidazole-6,3'-disulphonate and
 3.5 parts of a reaction product of p-tert.octylphenol and ethylene oxide.

EMULSION CONCENTRATE

Easily soluble active substances were formulated as an emulsion concentrate in accordance with the following instruction:
 20 parts of active substance
 70 parts of xylene and
 10 parts of a mixture of a reaction product of an alkylphenol with ethylene oxide and calcium dodecylbenzenesulphonate are mixed. On dilution with water to the desired concentration, a sprayable emulsion resulted.

GRANULES 7.5 g of one of the active substances of formula I were dissolved in 100 ml of acetone and the acetone solution thus obtained was added to 92 g of granular attapulgite. The whole was well mixed and the solvent was stripped off in a rotary evaporator. Granules containing 7.5 % of active substance were obtained.

EXAMPLE 3

A. *Rhipicephalus bursa*

Batches of 5 adult ticks or of 50 tick larvae were counted out into a glass test tube and dipped for 1 to 2 minutes in 2 ml of an aqueous emulsion from a dilution series with 100, 10, 1 and 0.1 ppm of test substance respectively. The test tube was then closed with a standard cottonwool pad and inverted so that the active substance emulsion could be taken up by the cottonwool.

Evaluation took place after 2 weeks in the case of the adults and up to 2 days in the case of the larvae. 2 repeats were run for each experiment.

100 % destruction was found at the following limiting concentrations (ppm):

| Active Substance No. | Rhipicephalus bursa | |
|---|---|---|
| | Adult | Larvae |
| 2.1 | 5 | 5 |
| 2.2 | 0.5 | 0.5 |
| 2.3 | 5 | 5 |
| 2.4 | 5 | 5 |
| 2.7 | 10 | 50 |

B. *Boophilus microplus* (larvae)

Experiments were carried out with batches of 20 sensitive or OP-resistant larvae, with an analogous dilution series to that of Test A. (The resistance relates to the toleration of diazinone). 100 % destruction was found at the following limiting concentrations (ppm) after 2 weeks:

| Active Substance No. | Boophilus microplus (larvae) | |
|---|---|---|
| | OP-resistant | sensitive |
| 2.1 | 5 | 5 |
| 2.2 | 1 | 1 |
| 2.3 | 5 | 5 |
| 2.4 | 5 | 5 |
| 2.7 | 50 | 10 |

C. *Dermanyssus gallinae*

The test was carried out analogously to Method A but with 20 mites. The evaluation took place after 72 hours.

100 % destruction was found at the following limiting concentrations (ppm):

| Active Substance No. | Dermanyssus gallinae |
|---|---|
| 2.1 | 100 |
| 2.2 | 100 |
| 2.3 | 100 |
| 2.4 | 100 |
| 2.7 | 50 |

EXAMPLE 4

Action against spider mites.

Bush bean plants (Phaseolus vulgaris) in the two-leaf stage, were infected with spider mites, 12 hours before the treatment with the active substance, by placing attacked pieces of leaf from a culture on them, so that after the expiration of this time a population in all stages of development was present on the plant. The plants were then sprayed with the emulsified active substance, with the aid of a chromatography atomiser, until a uniform deposit of droplets was formed on the top surface of the leaf. After 2 and 7 days, the results were evaluated: the plant parts were inspected under a stereo-microscope for calculation of the percentages of destruction. The effect on eggs was not yet ascertainable after 2 days with this experimental arrangement, because the average hatching time was not yet accurately known at this point in time.

The table which follows gives the percentages of destruction of the normally sensitive variety Tetranychus urticae Koch and the percentages of destruction of the phosphoric acid ester-tolerant variety Tetranychus telarius L.

Active Substance No. 2.3
a. Action against Tetr. urticae

DESTRUCTION IN PERCENTAGES

| | after 2 days | | | after 7 days | |
|---|---|---|---|---|---|
| Conc. [ppm] | Larvae | Adults | Eggs | Larvae | Adults |
| 800 | 100 | 100 | 100 | 100 | 100 |
| 400 | 100 | 100 | 100 | 100 | 100 |
| 200 | 100 | 100 | 60 | 80 | 100 |
| 100 | 80 | 100 | 0 | 60 | 80 |

Active Substance No. 2.3
b. Action against Tetr. telarius

DESTRUCTION IN PERCENTAGES

| | after 2 days | | | after 7 days | |
|---|---|---|---|---|---|
| Conc. [ppm] | Larvae | Adults | Eggs | Larvae | Adults |
| 800 | 100 | 100 | 80 | 100 | 100 |
| 400 | 100 | 100 | 80 | 100 | 100 |
| 200 | 100 | 100 | 60 | 60 | 100 |
| 100 | 80 | 100 | 0 | 0 | 80 |

I claim:

1. The compound of the formula

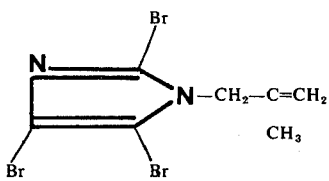

2. The compound of the formula

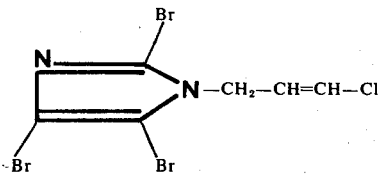

3. The compound of the formula

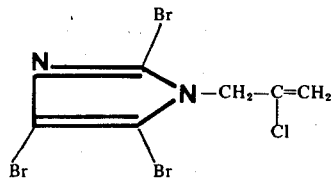

* * * * *